(12) United States Patent
Kipke et al.

(10) Patent No.: US 9,014,796 B2
(45) Date of Patent: Apr. 21, 2015

(54) FLEXIBLE POLYMER MICROELECTRODE WITH FLUID DELIVERY CAPABILITY AND METHODS FOR MAKING SAME

(75) Inventors: Daryl R. Kipke, Dexter, MI (US); David S. Pellinen, Ann Arbor, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 2222 days.

(21) Appl. No.: 11/452,551

(22) Filed: Jun. 14, 2006

(65) Prior Publication Data

US 2006/0282014 A1 Dec. 14, 2006

Related U.S. Application Data

(60) Provisional application No. 60/690,274, filed on Jun. 14, 2005.

(51) Int. Cl.
*A61B 5/04* (2006.01)

(52) U.S. Cl.
CPC ....... *A61B 5/04001* (2013.01); *A61B 2562/125* (2013.01)

(58) Field of Classification Search
USPC ................................. 600/544–545
See application file for complete search history.

(56) References Cited

U.S. PATENT DOCUMENTS

| | | | |
|---|---|---|---|
| 3,847,687 A | 11/1974 | Davidsohn et al. | |
| 3,921,916 A | 11/1975 | Bassous | |
| 4,461,304 A | 7/1984 | Kuperstein | |
| 4,904,237 A | * 2/1990 | Janese | 604/28 |
| 5,207,709 A | 5/1993 | Picha | |
| 5,215,088 A | 6/1993 | Normann et al. | |
| 5,308,442 A | 5/1994 | Taub et al. | |
| 5,385,635 A | 1/1995 | O'Neill | |
| 5,464,404 A | * 11/1995 | Abela et al. | 606/15 |
| 5,585,827 A | 12/1996 | Murakami | |
| 5,588,597 A | 12/1996 | Reinecke et al. | |
| 5,843,150 A | 12/1998 | Dreessen et al. | |
| 5,927,277 A | 7/1999 | Baudino et al. | |
| 5,938,694 A | 8/1999 | Jaraczewski et al. | |
| 5,975,085 A | 11/1999 | Rise | |
| 5,989,445 A | 11/1999 | Wise et al. | |
| 5,992,769 A | 11/1999 | Wise et al. | |
| 6,006,124 A | 12/1999 | Fischell et al. | |
| 6,016,449 A | 1/2000 | Fischell et al. | |
| 6,044,304 A | 3/2000 | Baudino | |
| 6,181,569 B1 | 1/2001 | Chakravorty | |
| 6,205,361 B1 | 3/2001 | Kuzma et al. | |

(Continued)

FOREIGN PATENT DOCUMENTS

| | | |
|---|---|---|
| WO | WO-01/12115 A1 | 2/2001 |
| WO | WO-01/97906 A2 | 12/2001 |

(Continued)

OTHER PUBLICATIONS

International Search Report for PCT/US 06/23139 (2 pages).

(Continued)

*Primary Examiner* — Michael D'Angelo
(74) *Attorney, Agent, or Firm* — Harness, Dickey & Pierce, P.L.C.

(57) ABSTRACT

A flexible multi-modal microelectrode is provided that combines multi-channel fluidic and electrical interfaces for biological and other systems. Methods of making and using same are also disclosed.

20 Claims, 11 Drawing Sheets

(56) References Cited

U.S. PATENT DOCUMENTS

| | | | |
|---|---|---|---|
| 6,208,881 B1* | 3/2001 | Champeau | 600/374 |
| 6,228,111 B1 | 5/2001 | Tormala et al. | |
| 6,324,433 B1 | 11/2001 | Errico | |
| 6,374,143 B1 | 4/2002 | Berrang et al. | |
| 6,430,443 B1 | 8/2002 | Karell | |
| 6,600,231 B2 | 7/2003 | Tominaga | |
| 6,618,623 B1 | 9/2003 | Pless et al. | |
| 6,834,200 B2 | 12/2004 | Moxon et al. | |
| 6,878,643 B2 | 4/2005 | Krulevitch et al. | |
| 7,004,948 B1 | 2/2006 | Pianca et al. | |
| 7,006,859 B1 | 2/2006 | Osorio et al. | |
| 7,010,356 B2 | 3/2006 | Jog et al. | |
| 7,011,680 B2 | 3/2006 | Alt | |
| 7,051,419 B2* | 5/2006 | Schrom et al. | 29/594 |
| 7,089,059 B1 | 8/2006 | Pless | |
| 7,548,775 B2 | 6/2009 | Kipke et al. | |
| 2002/0198446 A1 | 12/2002 | Hill et al. | |
| 2003/0093129 A1 | 5/2003 | Nicolelis et al. | |
| 2003/0100823 A1 | 5/2003 | Kipke et al. | |
| 2004/0006264 A1 | 1/2004 | Mojarradi et al. | |
| 2004/0102828 A1 | 5/2004 | Lowry et al. | |
| 2004/0106169 A1 | 6/2004 | Evans | |
| 2004/0199235 A1 | 10/2004 | Younis | |
| 2005/0004627 A1* | 1/2005 | Gibson et al. | 607/57 |
| 2005/0021117 A1* | 1/2005 | He et al. | 607/116 |
| 2005/0137647 A1 | 6/2005 | Wallace et al. | |
| 2006/0247749 A1 | 11/2006 | Colvin | |
| 2006/0258951 A1 | 11/2006 | Bleich et al. | |
| 2006/0276866 A1* | 12/2006 | McCreery | 607/116 |
| 2006/0282014 A1 | 12/2006 | Kipke et al. | |
| 2007/0073130 A1 | 3/2007 | Finch et al. | |
| 2007/0123765 A1 | 5/2007 | Hetke et al. | |
| 2007/0135885 A1 | 6/2007 | Risi | |
| 2008/0208283 A1 | 8/2008 | Vetter et al. | |
| 2009/0102068 A1 | 4/2009 | Pellinen et al. | |
| 2009/0118806 A1 | 5/2009 | Vetter et al. | |
| 2009/0132042 A1 | 5/2009 | Hetke et al. | |
| 2009/0187196 A1 | 7/2009 | Vetter | |
| 2009/0234426 A1 | 9/2009 | Pellinen et al. | |
| 2009/0240314 A1 | 9/2009 | Kong et al. | |
| 2009/0248118 A1 | 10/2009 | Bradley et al. | |
| 2009/0253977 A1 | 10/2009 | Kipke et al. | |
| 2009/0299167 A1 | 12/2009 | Seymour | |
| 2009/0312770 A1 | 12/2009 | Kozai et al. | |
| 2010/0030298 A1 | 2/2010 | Martens et al. | |
| 2010/0145422 A1 | 6/2010 | Seymour et al. | |

FOREIGN PATENT DOCUMENTS

| | | |
|---|---|---|
| WO | WO-02/41666 A1 | 5/2002 |
| WO | WO-02/096482 A2 | 12/2002 |
| WO | WO-2008/038208 A2 | 4/2008 |
| WO | WO-2008/072125 A1 | 6/2008 |

OTHER PUBLICATIONS

U.S. Appl. No. 12/848,828, filed Aug. 2, 2010, Anderson.

PCT International Search Report of PCT/US2004/035030, mailed Feb. 21, 2005 (4 pages).

Seymour, John P., Kipke, Daryl R. "Neural probe design for reduced tissue encapsulation in CNS" Biomaterials 28 (2007) 3594-3607, Apr. 5, 2007 (14 pages).

Seymour, John P., Elkasabi, Yaseen M., Chen, Hsien-Yeh, Lahann, Joerg, Kipke, Daryl R., "The insulation performance of reactive parylene films in implantable electronic devices" Biomaterials 30 (2009) 6158-6167, Aug. 22, 2009 (10 pages).

Kaplan, et al., "A Novel Fabrication Method of Capillary Tubes on Quartz for Chemical Analysis Applications" IEEE Proceedings, Micro Electro Mechanical Systems, pp. 63-68, Jan. 25-28, 1994 (6 pages).

Lin, et al., "Silicon Processed Microneedles"; IEEE Journal of Microelectromechanical Systems, vol. 8, No. 1, Mar. 1999, pp. 78-84. (7 pages).

* cited by examiner

Di-para-xylylene (Dimer) → para-xylylene (Monomer) → Poly(para-xylylene) (Polymer)

1) Vaporize: 150 °C, 1.0 torr
2) Pyrolize: -680 °C, -0.5 torr
3) Deposit: 25 °C, 0.1 torr
-70 °C
0.001 torr Vaporizer — Pyrolsis — Deposition Chamber — Cold Trap — Mechanical Vacuum Pump

*Fig-12*

FLEXIBLE POLYMER MICROELECTRODE WITH FLUID DELIVERY CAPABILITY AND METHODS FOR MAKING SAME

CROSS-REFERENCE TO RELATED APPLICATIONS

This application claims the benefit of U.S. Provisional Application Ser. No. 60/690,274, filed Jun. 14, 2005, which is hereby incorporated by reference in its entirety.

TECHNICAL FIELD

The present invention relates to the field of microelectrodes and, more particularly but without limitation, to microelectrodes for research, diagnostic, and/or clinical use in biological or other systems.

BACKGROUND

The use of simple electrodes to sense bio-potentials has been going on for almost a century. Most of the early techniques relied on sharpened wires or glass micropipette electrodes. Sharpened wire electrodes are still widely used for neural recordings. They are fairly inexpensive and are simple to construct, yet are capable of recording multiple high quality action potentials from localized areas of tissue.

Although wire electrodes are extremely well-suited for neural recording, unless special equipment is used, the recording site is generally limited to the tip of the electrode. Metal electrodes tend to be hand-made, one-at-a-time, making it difficult to precisely control the surface roughness and amount of exposed conductor. The characteristic impedance, a good indicator of future electrode performance, is highly dependent on the state of the exposed site and can drift unpredictably with irregular surface characteristics.

Glass capillaries, drawn to a few microns and filled with an electrolyte, are commonly referred to as glass microelectrodes. Because the glass can be drawn to such small dimensions, they have generally been used as intracellular electrodes, measuring the potentials within (large) individual cells. These electrodes are also easily adaptable to measuring extracellular potentials.

Similarly to wire electrodes, glass microelectrodes are typically hand-made, one-at-a-time. Unlike the cone electrode where the recording electrode is inside the tube with active neurites, the recording site of a typical glass microelectrode is generally at the tip of the electrode, where the internal electrolyte contacts the outside fluid of the electrode. The opening typically varies from electrode to electrode, and the tip tends to get clogged, making the electrode less sensitive.

Near the beginning of the age of the semiconductor integrated circuit, researchers started using batch fabrication techniques and tools developed in silicon foundries to micromachine a variety of bioprobes out of a wide variety of materials. While non-lithographically produced electrodes are ideal for many applications, BIO-MEMS neural interfaces produced by batch fabrication methods common to the semiconductor industry have several advantages, including low cost once mass-produced, high yield, high channel counts, accurately controlled dimensions (for site spacing and geometry) and little variability from electrode to electrode, batch to batch.

The availability of a wide variety of processes and tools specialized for the fabrication of silicon integrated circuitry made silicon a good choice for some of the earliest bioprobes. A variety of silicon-containing composite substrates such as SOI (silicon-on-insulator), silicon nitride with silicon, and polysilicons, have also been tried to varying degrees of success. Ceramic substrates have the advantages of high insulation resistance and no need for expensive cleanroom equipment. Some rugged substrate materials such as molybdenum were tried, but typically were not suitable for chronic usage because of insulation coating problems.

Studies with microelectrode electrical recordings alone can only provide information about local potentials and possible source distributions within biological systems. Therefore, to begin to fully understand complex behavior, it is desirable to be able to deliver precise amounts of chemicals to localized areas while monitoring the system's electrical responses in vivo.

A significant amount of research has been conducted on the micromachining of hypodermic microneedles designed for drug delivery. The advantages of micromachining these needles include small size, reproducibility, low unit cost, and the potential integration of sensors, pumps, and other microaccessories. Microneedles have been batch-fabricated from a variety of materials, including glass, silicon-silicon nitride, polysilicon, polymers and metal. However, most of these electrodes are meant only for drug delivery and will not simultaneously record action potentials.

The promise of advanced microelectrode systems to significantly improve the quality of life for the impaired hinges on the development of an efficacious and safe implant to interface with the tissue over extended periods. Despite the wide range of materials available and the increasing complexity of the design process, there still exist a number of fundamental problems associated with drug delivery microelectrodes and microelectrode arrays. The largest failure modes for chronically implanted electrodes are thought to be the inflammation of tissue due to the microelectrode, and micromotion-induced trauma. While batch-fabricated BIO-MEMS electrodes offer many advantages over wire electrodes due to the wide choice of biocompatible materials, reliable interconnects and sophisticated processing schemes, the failure modes of the electrodes largely remain the same. Accordingly, there is a need for a reliable, consistent, and long-term microscale system for interfacing directly with biological systems which overcomes the shortcomings of previously developed systems.

SUMMARY

In some embodiments, without limitation, the present invention is directed to a flexible multi-modal microelectrode that combines multi-channel fluidic and electrical interfaces for biological systems, and is manufactured with a novel all-planar process that is compatible with standard planar-lithographic complementary field-effect transistor (CMOS) techniques. Some embodiments of the invention comprise a thin-film polymer-based substrate that is flexible and can be shaped and formed to follow 3-dimensional contours of the biological system. Multiple fluidic ports and channels, as well as electrode sites, can be precisely placed on a single device for localized drug-delivery and/or sampling, in addition to recording and/or stimulation. The fabrication process used to form these devices and the fluidic channels within the devices is unique. The device may optionally include a plurality of electrical contacts, be multi-shanked, and may contain an integrated polymer cable which provides for efficient contact points for a high-density connector. The device can be readily connected to bond pads and fluidic ports and is compatible with the "Intracranial Neural Interface System", as described in Published U.S. Patent Application no. 2005/0143790, which is hereby incorporated by reference in full.

Until now, similar multifunctional (e.g., recording/stimulating/drug delivery) were not flexible. One particular advantage of a flexible polymer electrode like the present invention is that it may be able to naturally conform to physical features and, therefore, less invasively reach localized targets deep within sulci of the human brain. Microfluidic drug delivery via a flexible micro-machined hybrid electrode can be used to supply a point source delivery of bioactive agents. The utility of the device is realized by coupling drug delivery with selective electrical stimulation while providing feedback of the efficacy via recording sites.

Microelectrodes comprising the invention are produced in a unique, all-planar surface micromachining process. They consist of a multi-layered parylene substrate with one or more layered metal film bond pads, recording sites, and interconnecting lines. Without limitation to any particular embodiment, the device is preferably made with five to seven parylene layers and at least two interleaved metallic layers arranged to form the housing for adding functionality (e.g. polymer valve) within the channel lumen outlet. The interleaved metals also act as in-process etch stops for the formation of self-aligned three dimensional structures. To facilitate recording, a top layer of patterned metal is used for the recording/stimulation sites, so that the sites are placed at the electrode surface. Other sites can be recessed within the electrode by the thickness of several of the parylene layers. Post-production site modifications include electro-plating with metals such as platinum black and the galvanostatic growth of conductive polymers such as polypyrrole ("PPY") or polyethylenedioxythiophene ("PEDOT"). These types of site modifications, along with select bioactive coatings, allow for post-process control of site recording characteristics.

In accordance with one embodiment, the present invention comprises a microelectrode with at least one electrode site of the microelectrode between at least two layers of a multi-layer parylene substrate and at least one channel for fluid delivery extending longitudinally from a proximal section of the device to a more distal section. In accordance with a further aspect of the present invention, the electrode(s) is located on a shaft of the microelectrode and the device can then be connected to other externally located equipment to additional perform its intended uses.

In another embodiment of the present invention, without limitation, a method of making a microelectrode with a fluidics microchannel is presented which comprises the steps of growing a sacrificial oxide on a silicon carrier; applying a first parylene layer; depositing and etching a first conductive metallization layer; applying a second parylene layer; masking and dry etching to create a microchannel; applying a third parylene layer; filling the microchannel with a sacrificial resist; apply a fourth parylene layer; depositing and etching a second metallization layer; applying a fifth parylene layer; and performing reactive ion etching to open and/or prepare desired locations. The microelectrode may then be released from the carrier by dissolving the oxide layer and be further processed and/or used for its desired purposes.

BRIEF DESCRIPTION OF THE DRAWINGS

The features and inventive aspects of the present invention will become more apparent from the following detailed description, the appended claims, and the accompanying drawings, of which the following is a brief description:

DETAILED DESCRIPTION

Referring now to the drawings, illustrative embodiments are shown in detail. Although the drawings represent the embodiments, the drawings are not necessarily to scale and certain features may be exaggerated to better illustrate and explain an innovative aspect of an embodiment. Further, the embodiments described herein are not intended to be exhaustive or otherwise limiting or restricting to the precise form and configuration shown in the drawings and disclosed in the following detailed description.

The present invention is directed to a flexible polymer recording/stimulating microelectrode with fluid delivery capabilities and to a fabrication process for same that integrates a flow channel in the design. This thin-film polymer-based substrate is flexible and can be shaped and formed to follow 3-dimensional contours of the biological system. Multiple fluidic ports and channels, as well as electrode sites, can be precisely placed on a single device for localized drug-delivery and/or sampling, in addition to recording and/or stimulation.

The fabrication process used to form the present device and the fluidic channels within the device is unique. In some embodiments, without limitation, the device may also include a plurality of electrical contacts, be multi-shanked, and may contain an integrated polymer cable which provides for efficient contact points for a high-density connector. The device can be readily connected to through bond pads and fluidic ports and is compatible with the "Intracranial Neural Interface System", as described in US Patent US2005/0143790. Fluids deliverable according to the present invention include, but are not limited to, drugs and other fluids for research, diagnostic and clinical applications.

Figure 1:
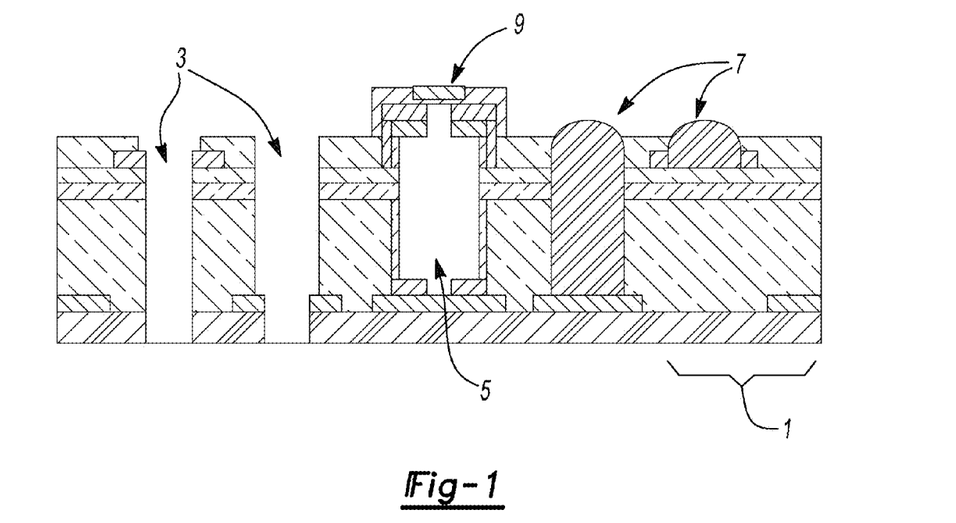
FIG. 1 is an illustrative cross-sectional view of one embodiment of the present invention. The cross-section is a composite showing inner details of the back end (bonding pads), recording/stimulation sites (front end) and channel (entire length of device, with outlet near recording sites).

FIG. 1 illustrates a cross-section of one embodiment of the device 1, showing the features of the bonding area 3, the channel 5, and recording/stimulating sites 7. The cross-section is a composite showing inner details of the wire bonding pads (back end), recording/stimulation sites (front end), and channel (entire length of device, with outlets near recording sites). Optionally a valve flap 9 may be included in some embodiments.

Figure 2A:
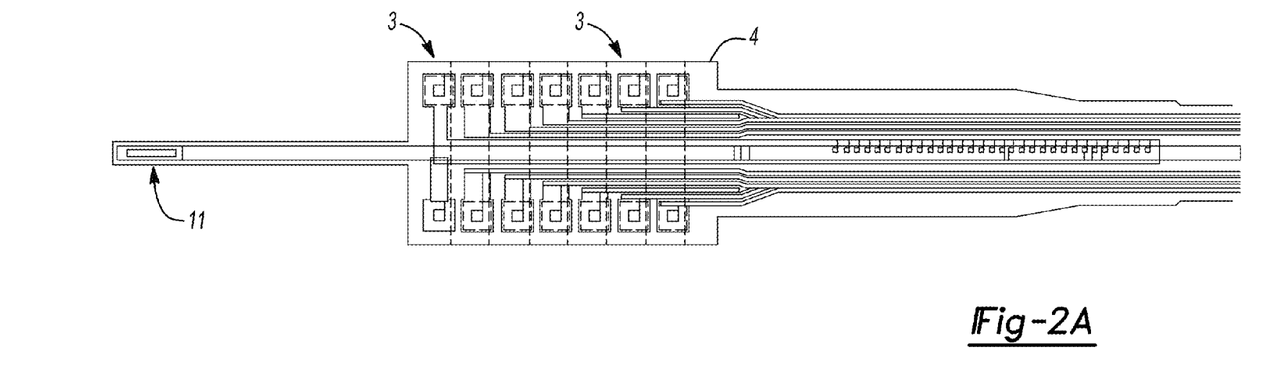
FIGS. 2(A)-(B) is a top plan view of the device shown in FIG. 1, showing at (A) a portion of the proximal end of the microelectrode, and (b) a portion of a distal segment of the microelectrode comprising the tip.
Figure 2B:
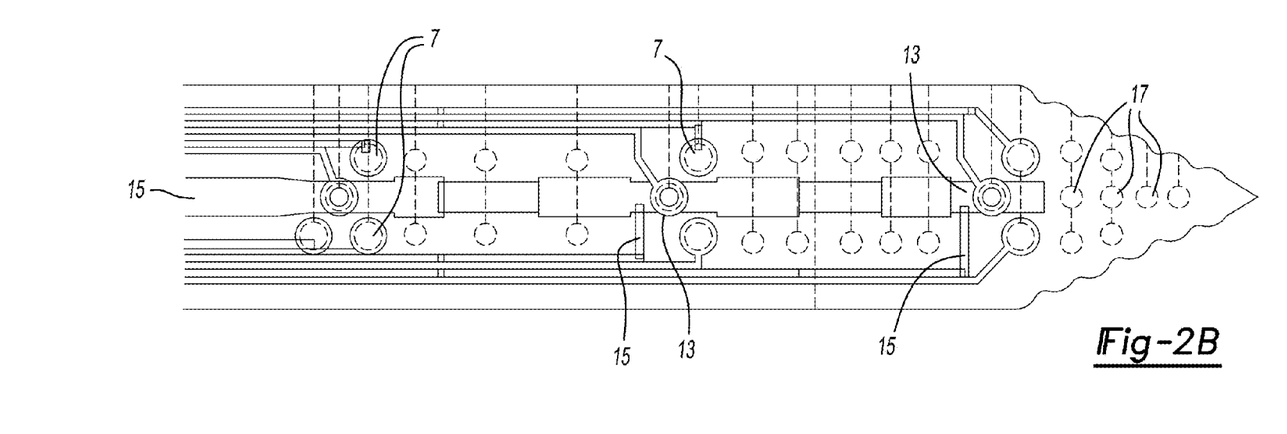

FIG. 2 illustrates additional details of some embodiments. These illustrations are derived from overlayed mask definitions (not shown), which are the actual lithographic masks used to manufacture the device. A fluid inlet 11 and one or more fluid outlets 13 are depicted, along with multiple pores 17 and recording sites 7, and optional valve control lines 15. The fluid inlet 11 permits connection to an external fluid source for delivery as desired through one or more fluid outlet 13.

Without limitation, FIGS. 3(A) and (B) illustrate an exemplary fabrication process for some embodiments of the present device, and are explained below. FIG. 4 shows actual device pictures, with dimensions and parts of some embodiments annotated.

To facilitate and assess electrode functionality, some embodiments of the present invention are designed to use similar chronic printed circuit boards ("PCB's"), connectors and recording system as the silicon electrodes that have been developed at the University of Michigan. (See e.g., Chen, J., K. D. Wise, et al. (1997), "A multichannel neural probe for selective chemical delivery at the cellular level," *IEEE Trans Biomed Eng* 44(8): 760-9, which is hereby incorporated by reference in full.) Connections from the device to the PCB are made with wire bonds. Engineering trade-offs (e.g., compromises on device dimensions) have been made to accommodate the needs of the end-users with the requirement for a repeatable, high-yielding manufacturing process. Although exemplary dimensions are included, the device may be made in other lengths, widths, and thickness, and the particular features of the device (as one example only, interconnecting lines) may be adapted similarly. Thus, in exemplary embodiments, without limitation, we have set the minimum metal dimension at about 6 µm to facilitate accurate etching on parylene surfaces, which can be "rough", depending on the state of the parylene-C reactor. The device thickness and microchannel height is determined by the thickness of the individual parylene layers. The device width (e.g., about 340 µm) can be decreased in consideration of the ability of the devices to resist delamination.

Figure 3A:
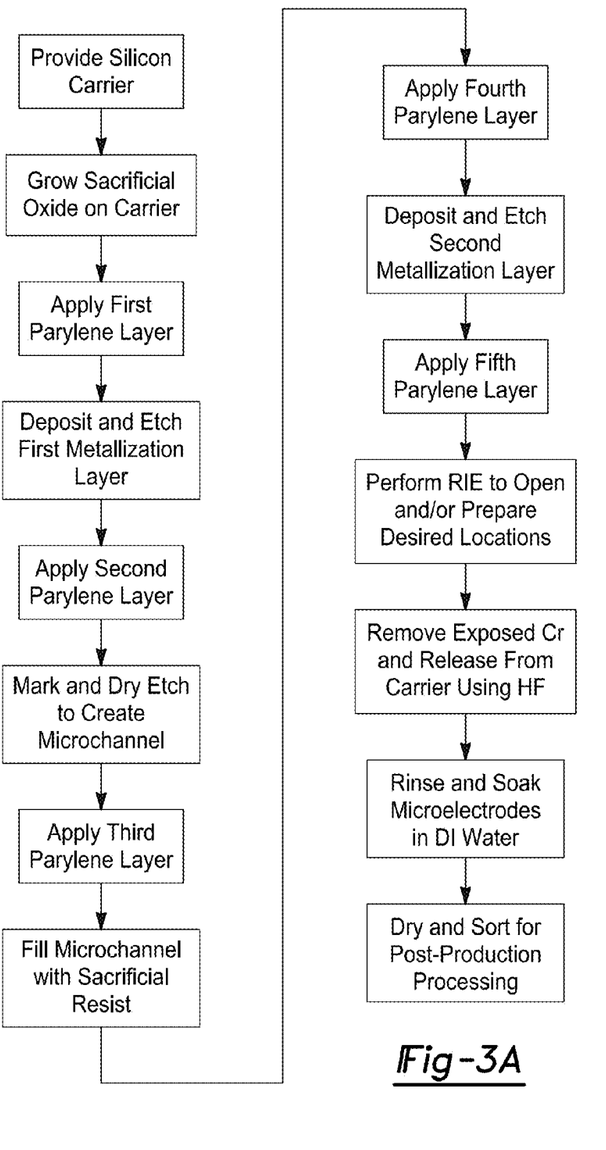
FIGS. 3(A)-(B) are flowcharts showing the basic steps in an exemplary method of making one embodiment of the present invention.
Figure 3B:
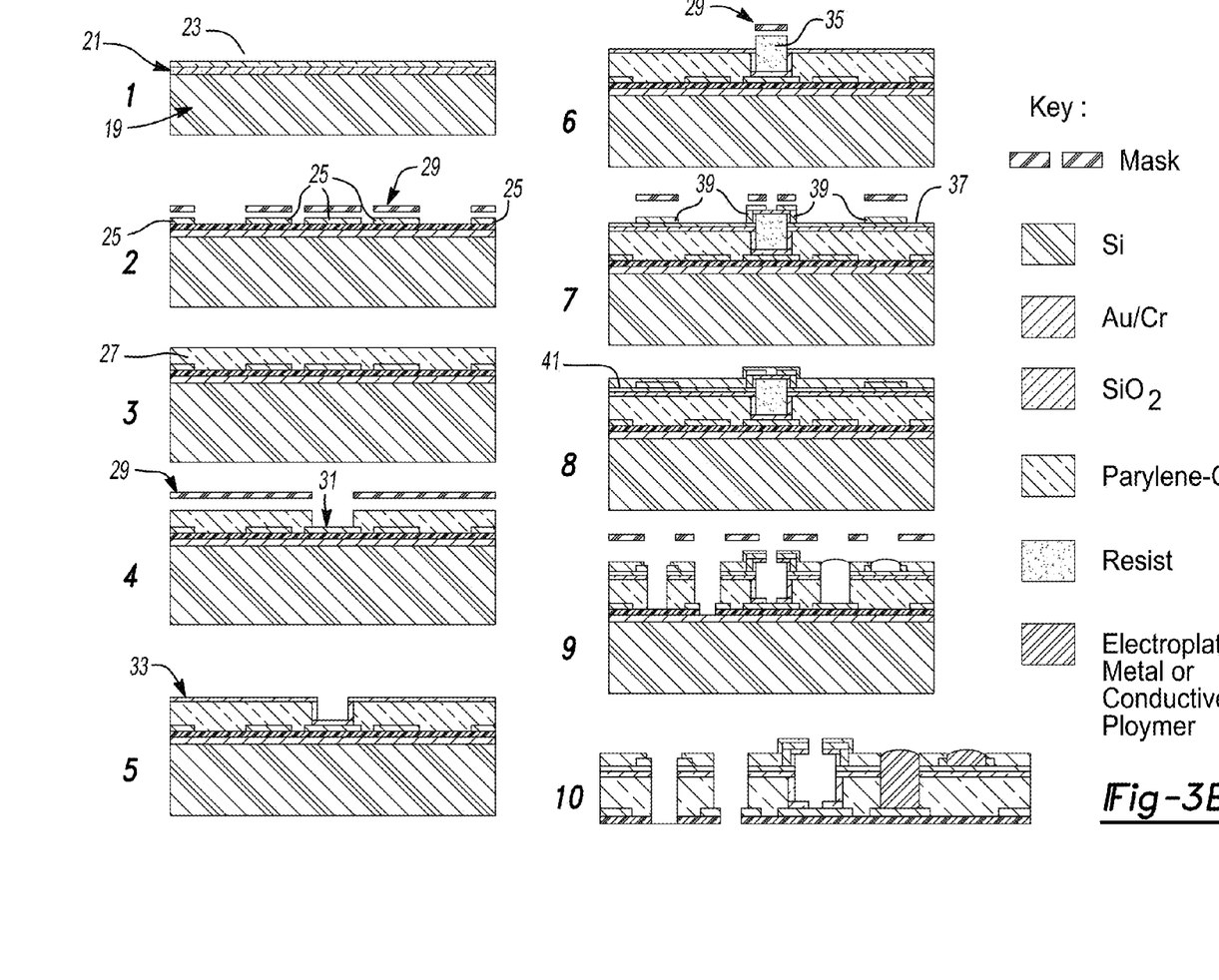
Figure 4A:
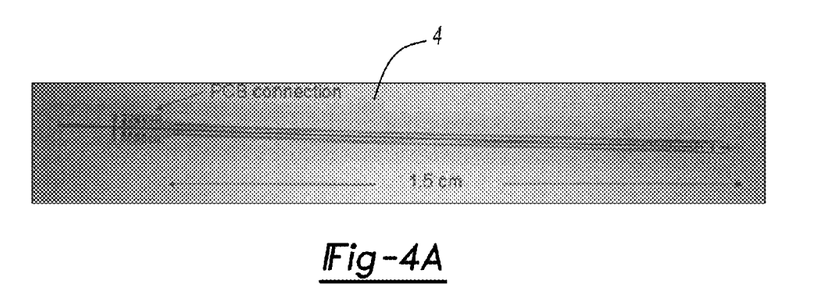
FIG. 4 is three top views of a single shank, single channel device in accordance with the present invention.
Figure 4B:
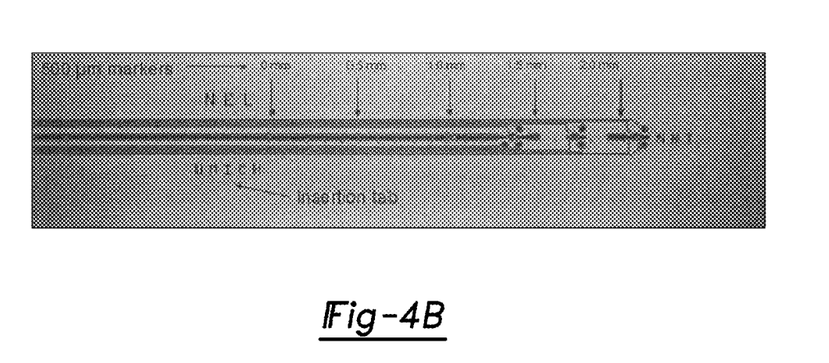
Figure 4C:
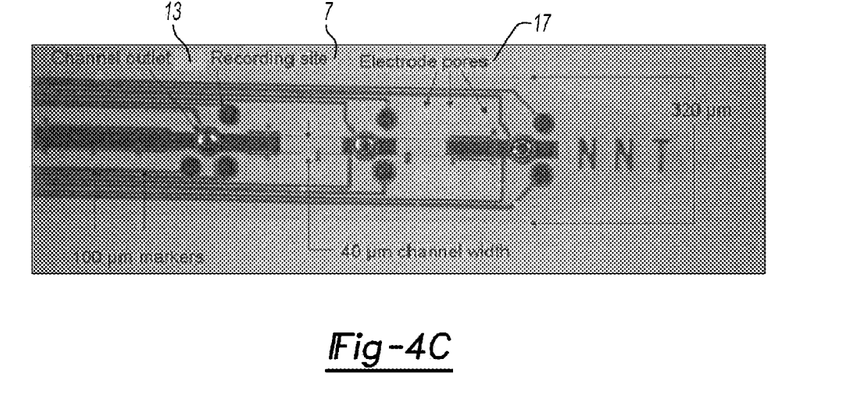

Flowcharts showing a method of making a microelectrode comprising the invention are shown at FIGS. 3(A)-(B). Generally a sacrificial oxide is first grown on silicon carrier wafers prior to parylene deposition. After the devices are fully fabricated, this oxide release layer is dissolved in hydrogen fluoride ("HF"), allowing the devices to float away freely. This results in less damage than mechanical release methods, while allowing increased device density on the wafer. After several rinses and soaks in deionized water, the devices are dried and are ready for bonding, plating, and other post-production processing.

Two layers of etched gold conductors, with a surrounding chrome or titanium adhesion layer, are inlayed within the polymeric structures to provide the recording sites, bond pads, interconnects, and valve control lines. A double metal deposition scheme is utilized to allow more densely packed lines on the narrow devices. The device bonding pads have pad arrangements that line up to the supporting PCB. These PCBs are of designs known to those of ordinary skill in the art similar to that currently used for the University of Michigan silicon puffer electrodes. (Chen, J., K. D. Wise, et al. (1997). "A multichannel neural probe for selective chemical delivery at the cellular level." *IEEE Trans Biomed Eng* 44(8): 760-9.) Recording and control sites are finished with a top layer of metallization, electroplated gold/platinum, or with electrically grown conductive polymers.

As shown in FIG. 3(B), panel 1, the process starts with 100 cm P-type <100> silicon wafers 19, pictured as the large bottom rectangle in all but the last panel. The cross-section shown is a composite showing inner details of the wire bonding pads (back end), recording/stimulation sites (front end) and channel (entire lenth of device, with outlet near recording sites). The first fabrication step (panel 1) is to grow a thermal oxide 21 shown as a thin layer on the surface of the wafer. This thermal oxide (about 1 µm) is grown by chemical vapor deposition ("CVD") in a high temperature furnace supplied with an oxygen source, and later dissolved for final release of the completed devices.

A chemical vapor deposition ("CVD") process is used to apply a first layer of parylene-C 23 (Special Coating Systems) (top layer on panel 1 of FIG. 3(B)), using an adhesion promoter (AZ 174)(not shown) to firmly anchor the first parylene layer to the oxidized substrate. It is also recommended that subsequent parylene layers also use the adhesion promoter. The first layer is grown to about 3 µm thick. Specialty Coating System's PDS-2010 parylene deposition system is used to grow all 5-7 parylene layers used in the process, although other systems known to those or ordinary skill may be suitable.

Figure 12:
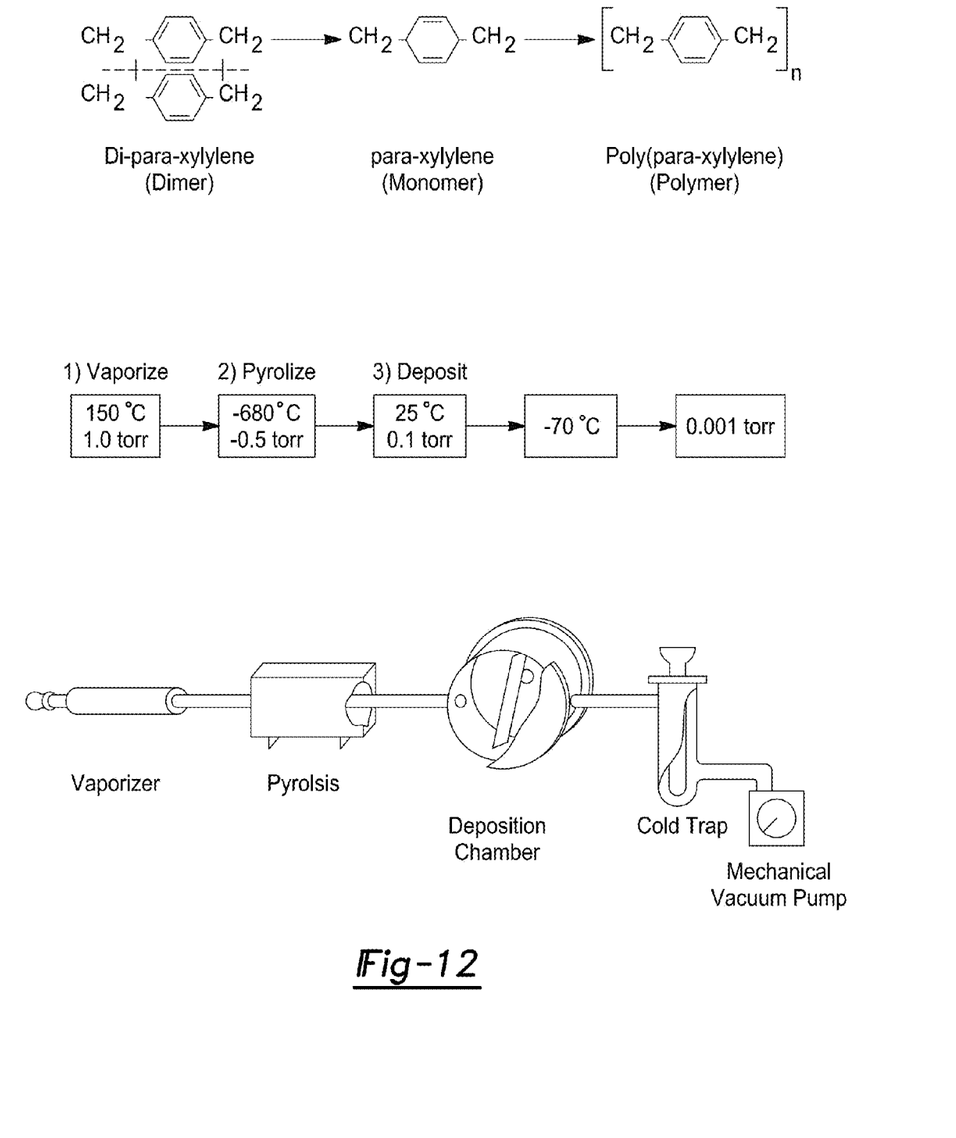
FIG. 12 shows a block diagram of the PDS-2010, Specialty Coating Systems, Inc., parylene deposition that is used, without limitation, in making the embodiments of the present invention.

FIG. 12 generally shows a parylene deposition system in accordance with the invention. Parylene is applied at room temperature with deposition equipment that controls the coating rate and ultimate thickness. Polymer deposition takes place at the molecular level:

Beginning with the granular form of parylene, raw material dimer, the material is vaporized under vacuum and heated to a dimeric gas.

The gas is then pyrolized to cleave the dimer to its monomeric form.

In the room temperature deposition chamber, the monomer gas deposits as a transparent polymer film.

The required thickness of a coating can vary based on the application, but thickness can range from the hundreds of angstroms to several mils, with the typical coating being in the microns range. (e.g., www.scscookson.com)

The second panel of FIG. 3(B) shows the application of a first metallization layer 25. During this step, Chromium ("Cr")/gold ("Au")/chromium ("Cr") (about 0.03 µm/0.3 µm/0.03 µm) is deposited and etched for use as a channel etch stop, lower recording sites and lower bonding pads. The metal is applied with an electron beam evaporation system, which evaporates metal in an evacuated chamber into which the wafers are mounted. After the metal is applied, it is photolithographically defined with the mask 29 shown in panel 2, and etched into the desired pattern using a variety of metal etchants. The estimated sheet resistance of the metal using the above thicknesses is about 0.07 ohm/square. Cr, when used, will not be exposed once fabrication is complete. A final Cr etch will ensure that the only exposed metal is Au.

The third panel of FIG. 3(B) shows the deposition of the second parylene-C layer 27. Deposition conditions for this and subsequent parylene layers are similar to the conditions for the first layer. The thickness (about 4-20 µm) of this layer determines channel depth. Due to current PDS-2010 limitations (~5 µm per deposition), the layer may take several independent depositions to reach full thickness.

The fourth panel of FIG. 3(B) shows the masking 29, then dry-etch of the channel in oxygen plasma, using the metal channel bottom 31 as an etch stop. The etch is accomplished with a reactive ion etcher (RIE) at low power levels (about <100 watts, to prevent mask and subsequent channel damage). A metal mask anchored to the initial parylene with a thin (about <2 µm) layer of photoresist is used to ensure that only the channel is etched. The metal mask is durable during the etching process, resulting in accurately defined features. The photoresist mask anchoring layer prevents plasma streaming under the metal during the etch. If this layer was omitted the device features would be over-etched and distorted. The oxygen plasma etch is terminated at the channel bottom metal interface, which functions as an etch stop.

The fifth panel of FIG. 3(B) illustrates deposition of a third parylene-C layer 33. This conformal polymer layer (about 1-3 µm) is used to form the bottom and sidewalls of the channel. The sixth panel of FIG. 3(B) shows the filling of the channel with a sacrificial resist 35. This is a photoresist similar to that which is used to photolithographically define structures throughout the process. In this embodiment, though, without limitation, the photoresist used (SP1827) was chosen due to its ability to fill the channel to the top while keeping the surface relatively planar. Since this is positive, the mask 29 only covers the channel; the bulk of the resist covering the wafer is removed.

The seventh panel of FIG. 3(B) shows the deposition of a fourth parylene-C layer 37. This polymer layer (about 1-3 µm) is used to form the channel top and sidewalls. Although the final device has a three dimensional profile, the device profile is kept planar throughout the process. This makes photolithographic processing easier. A second layer of metallization 39, preferably of same thickness and composition as before, is deposited and etched in a similar manner to form the upper bonding pads, upper sites, and concentric ring around channel outlets. The lithographic mask used for this metal layer is aligned over the previous layers to form self-aligning etch stops. These etch stops are used during the final etch, allowing for sizing of the channel outlet.

The eighth panel of FIG. 3(B) shows the deposition of a fifth layer of parylene-C 41. This polymer layer (about 1-3 µm) is used to form the top insulating layer of this embodiment of the device.

Panel nine of FIG. 3(B) shows the final RIE which opens recording sites (Au etch stop), opens bonding pads (Au/Silicon ("Si") etch stops), opens channel inlet/outlets (Au etch stops), and prepares the outlet ports for lower and upper site recording, or valve flap placement (the latter not shown). All of the final features to be etched out, including pressure-operated flap valves, recording/stimulating sites and bond pads, are defined by the final photolithographic mask. These mask features are transferred to a metal layer (typically aluminum) that ensures that only the excess polymer is removed. An oxygen plasma is used to accomplish the etch. Once the etch is complete, the aluminum is stripped away with a commercial etchant, leaving distinct, contoured, three-dimensional structures. After this step, the exposed Cr from the wafers is removed with commercially available etchant, leaving only Au exposed at the site. Final panel 10 of FIG. 3(B) shows the results from clearing the channel of the sacrificial photoresist layer using acetone, followed by a rinse with isopropyl alcohol ("IPA"). The structures then released from the silicon base using HF. The HF dissolves the silicon dioxide release layer within minutes, allowing the structures to float freely. The microelectrodes are then thoroughly rinsed and soaked in deionized water at least three times. After this, the microelectrodes are ready for drying, sorting, and bonding.

The post-processing steps start with wire bonding 3 through a PCB connection 4 to a PCB (not shown), followed by microfluidic connection to polymer tubing and flow verification in the newly created channel. External fluid connections to the device are made by attaching polymer tubing over the probe inlet (See FIG. 2 for probe inlet). Once flow has been verified, a connector is soldered on the PCB. Delicate portions of the PCB/microelectrode interface are then covered with epoxy and finally silicone elastomer, which is used to prevent damage to the microelectrode if it is pushed up against the hard PCB. In cases where electrode sites are recessed within the microelectrode by the thickness of the parylene layers (especially sites formed by the first metal layer), a method is used to build up the site so that it reaches the microelectrode surface. Suitable methods include, among others, electroplating with platinum black and the galvanostatic growth of conductive polymers such as PPY or PEDOT. These methods are used instead of a third metal mask that could be used for site definition. These modifications of the site allow for certain post-process control of site recording characteristics by changing the site size and surface morphology, and therefore the site impedance.

EXAMPLES

The following examples of some embodiments of the invention are provided without limiting the invention to only those embodiments described herein.

Three examples are given that demonstrate the functionality of exemplary embodiments of the present invention. These examples outline the different modes of operation, including electrical recording (similar in functionality to electrical stimulation), fluid delivery (similar in functionality to fluidic micro-sampling), and multimodal recording and fluid delivery. Each embodiment is capable of the aforementioned modes of operation.

Figure 10:
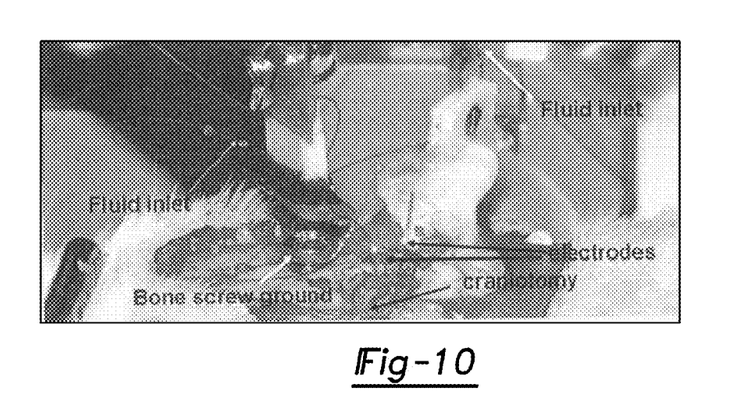
FIG. 10 shows a rat skull with two invented microelectrodes implanted during an acute surgery designed to validate the drug delivery capabilities of the electrode. The electrical ground is tied to the bone screw, which is in contact with CSF. Each microelectrode was separately tested for changes in electrical activity while locally injecting the excitatory neurotransmitter agonist, AMPA.

For all examples listed hereafter, the following procedures and methods were used. All examples listed were conducted in live rats as part of in vivo evaluation of the microelectrodes. Each rat was implanted with an electroplated microelectrodes and a 16-channel silicon microelectrode for comparison purposes. Both types of microelectrodes were implanted in the forelimb region of the motor cortex. The rats were implanted for 1 month, at which time the animals were sacrificed for histological analysis. A photograph taken during an implantation procedure is shown in FIG. 10.

Initial anesthesia was administered via an intra-peritoneal (IP) injection of a ketamine cocktail consisting of 50 mg/ml ketamine, 5 mg/ml xylazine, and 1 mg/ml acepromazine at an injection volume of 0.125 ml/100 g body weight. Updates of 0.1 ml ketamine [50 mg/ml] were delivered as needed during the surgery, approximately every hour.

Animals were secured to a standard stereotaxic frame and the cranium was exposed and cleaned. Three stainless steel bone screws were inserted into the skull. The microelectrodes' connectors were grounded to the bone screw that was over the parietal cortex using a stainless steel ground wire. A craniotomy, approximately 3×2 mm, was created over the target cortical area. Two incisions were made in the dura mater over the exposed area to create four flaps, which were then folded back over the edge of the craniotomy.

Insertion of the devices can be accomplished via several different methods. Because of the device flexibility, hand insertion was challenging. A silastic coated tab was placed 2 mm from the recording site at the tip. This tab was used for handling the microelectrode to help prevent damage to the device. After the dura was resected, the microelectrode was implanted by hand, similar to the process for implanting silicon microelectrodes. The tip of the microelectrode was designed to be sharp enough to pierce the pia mater. A mechanical insertion device to which the invention can be attached during insertion was developed to assist with the insertion process. The invention can be attached to a rigid "shuttle" and then released once inserted into the brain.

After insertion into the motor cortex, the forelimb cortex coordinates used were: 3.0 mm anterior to bregma, 2.5 mm lateral from midline, and 1.4 mm deep from the surface of the brain. The hindlimb cortex coordinates were: 1.5 mm posterior to bregma, 2.0 mm lateral from midline, and 1.4 mm deep from the surface of the brain. Next, a hydrogel was applied as a dural sealant. The integrated cables and printed circuit boards were covered in a silicone elastomer ("Kwik-Sil" by World Precision Inst.), all of which were then enclosed with dental acrylic (Co-Oral-Ite Dental Mfg. Co.) for additional protection, thus leaving the omnetics connector available to plug into. Finally, sutures were used to close the skin around the acrylic and anti-bacterial ointment was applied to this region. A final intraperitoneal injection of Buprenorphine at an injection volume of 0.01-0.05 mg/kg body weight was given for pain relief.

An initial impedance measurement for all sites was taken to ensure the mechanical and electrical integrity of the probes was still intact as well as to establish a baseline reading to compare to further results measurements. Initial neural unit activity was sorted and recorded using a Multi-Channel Neural Acquisition Processor (MNAP; Plexon Inc., Dallas, Tex.). The animals were then allowed to recover from the surgery for 48 hours.

Example 1

Neural Recordings

Figure 5:
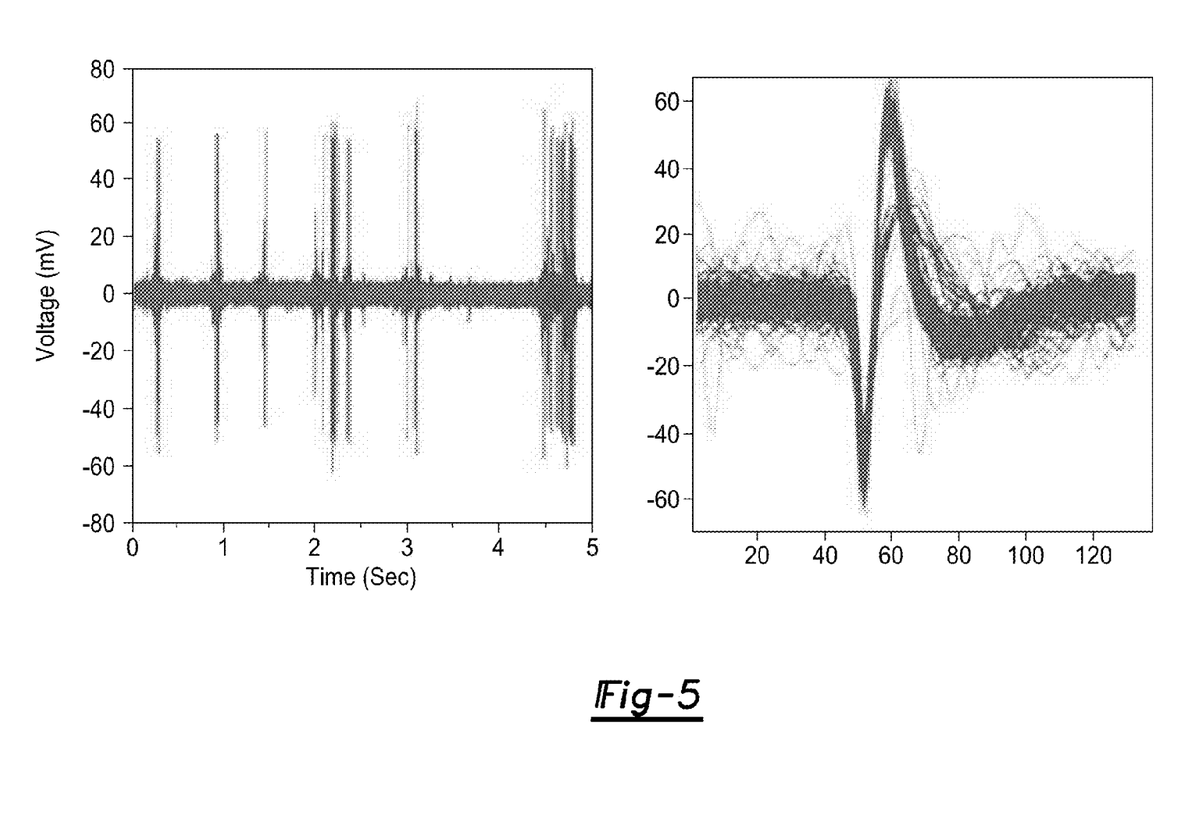
FIG. 5 is an example of the recording capabilities of a microelectrode made in accordance with the invention.
Figure 6:
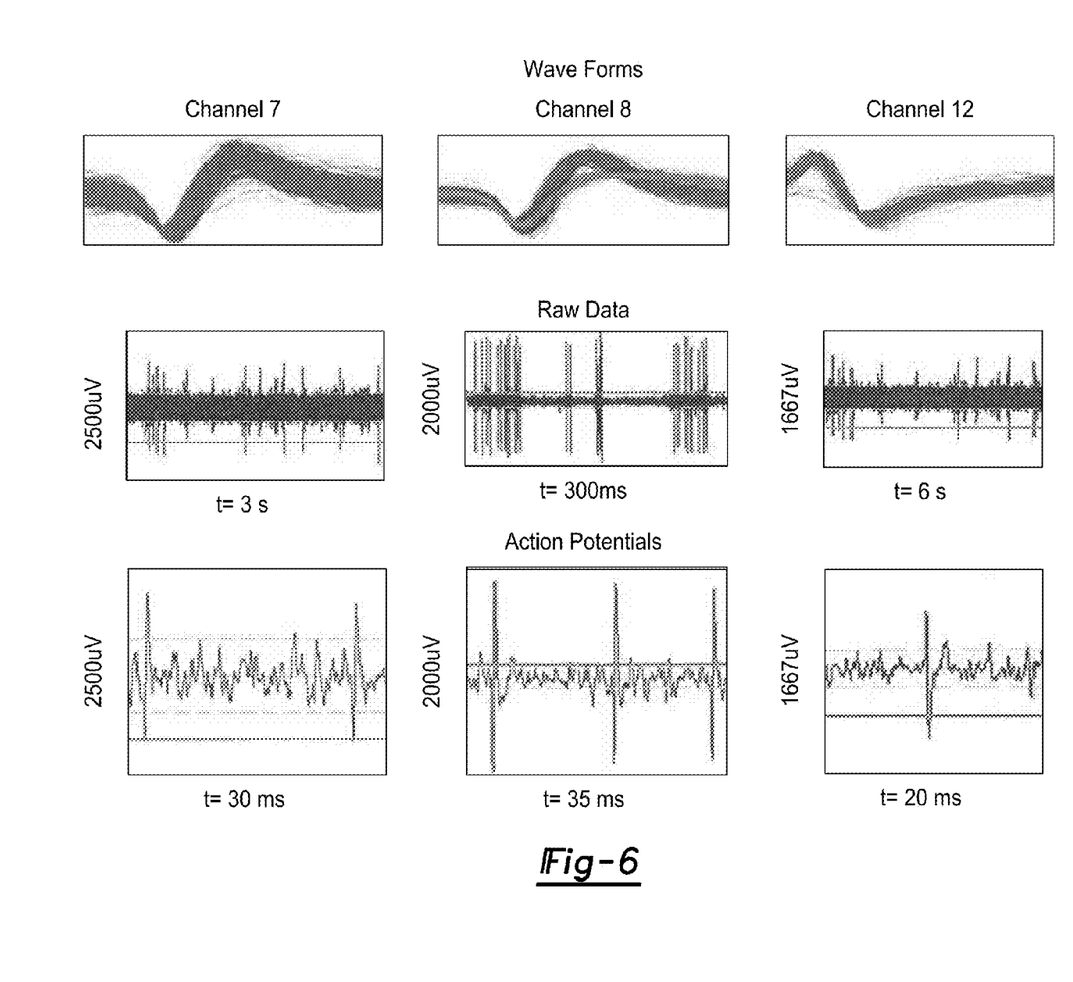
FIG. 6 shows the recording capabilities of one embodiment of the present microelectrode demonstrated with data snapshots: waveforms, raw data samples, and action potentials of 3 different units on 3 different channels on day four after the implantation for FP4.

Long-term viability of the microelectrodes, as well as the ability to record action potentials was evaluated in a series of experiments. Neuronal spikes were detected on all bonded channels and the activity of a single-unit was followed consistently out to for 8 days. FIGS. 5 and 6 show the recording capabilities of the invention. The picture to the left in FIG. 5 shows five seconds of unit activity from one of the recording sites soon after implantation. The sample shows spike activity to the left, and to the right a series of overlayed, thresholded action potentials recorded from rat cortex from one site of a parylene microelectrode array (site size 40×40 µm). These are normal firing patterns from the motor cortex while the rat is under anesthesia.

FIG. 6 shows data snapshots of 3 different spikes on 3 different channels several days after implantation. The data set includes waveforms, raw data samples, and action potentials. The data show simultaneous recording of at least three different spikes from three of the channels of the implanted device.

Electrical Viability Tests: A Keithley 2400 Sourcemeter was used to monitor leakage currents through the dielectric layers of a test probe. With 10 volts applied, no leakage current >5 nA (the instrument limit) was encountered during the one month test. Impedance spectroscopy measurements were taken with an Autolab® Electrochemical Measurement system, and were used to determine a microelectrode's suitability for implantation.

Figure 7:
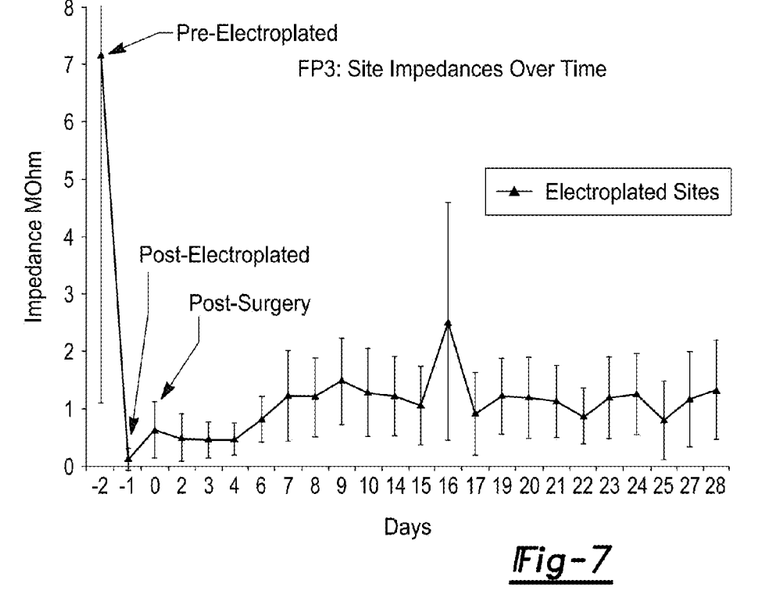
FIG. 7 shows impedance results for a rat implanted with an invented parylene substrate electrode during a 1 month period. Electroplated sites remained under 2 Megohms, while non-plated sites (not shown) retained their initial high impedance.

After implantation, the electrical tests were repeated to evaluate the tissue response to the implant and to continue monitoring the microelectrode itself for changes in its electrochemical properties. FIG. 7 shows the impedance results sampled at 1-kHz for a variety of recording sites. Bonded site #10, which was not electroplated, continued to show an impedance grater than 4 megohms for the duration of the test. The averaged impedance of the electroplated sites remained under 1 megohm for the duration.

Figure 8:
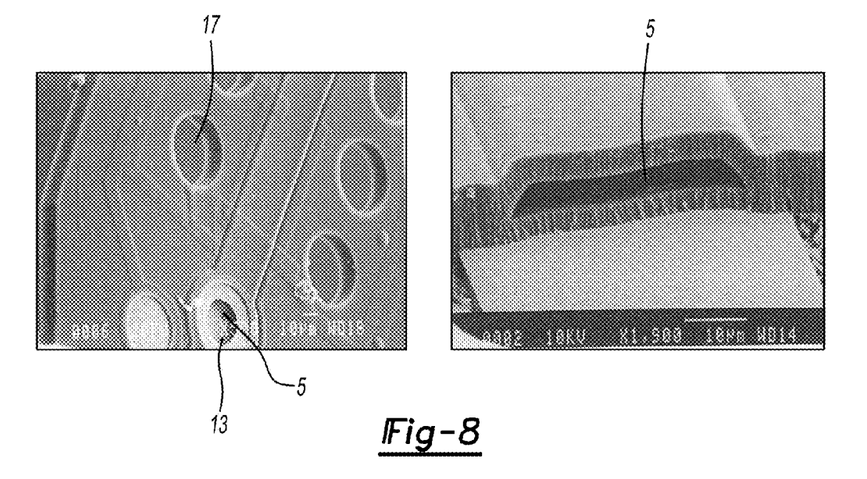
FIG. 8 shows views of segments of the microchannel comprising part of some embodiments: LEFT: an angled view showing a fluid outlet of the microchannel and some pores. Note the 40 μm channel running from the top to the channel outlet at the bottom of the picture. RIGHT: A cross-sectional view of the channel. Note that there are no visible indications of where one of the parylene layers ends and another begin, indicative of the structure's resistance to delamination.

FIG. 8 shows views of the channel that were built into the invented microelectrode, with metal electrode sites nearby. The dimensions of the channel are determined by the etching mask dimensions and individual polymer layer thicknesses. The metal etch-stops, and not the etch-time, control the depth of the channel. Note the relative width of the overall microelectrode compared to the narrower channel width. Some of this additional width is used to route interconnections, while some provides a structural feature for delamination resistance. Note the lack of delamination evidence in the right portion of FIG. 8 represented by the inability to distinguish between the different parylene layers.

Example 2

Fluid Delivery

Figure 9:
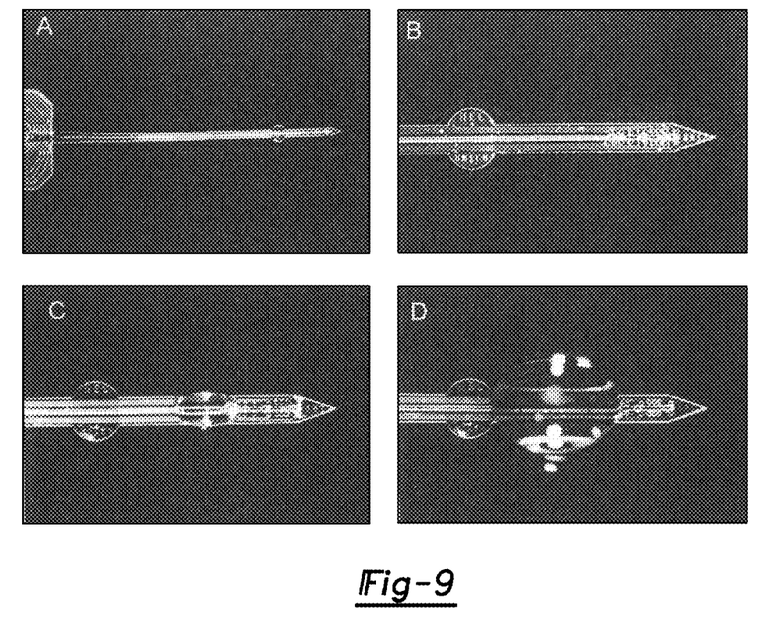
FIGS. 9(A)-(D) show manual pumping through a microelectrode comprising the invention. Figure A shows the whole electrode (about 1.5 cm long), up to the bonding pads. The fluid connection (not shown) is to the far left of the probe. Figure B shows the implantable portion of the microelectrode prior to fluid delivery. Figure C show the initiation of flow, which quickly develops into a large bubble of fluid in Figure D.

Extensive bench top test were conducted to evaluate the ability of the invented device to deliver precise amounts of fluids. The fluid was delivered via a computer-operated syringe-pump and connected micro-tubing. Various molecular dyes were loaded into the fluidic channel and injected into different medias. A High Performance Liquid Chromatography (HPLC) instrument and an Ultraviolet spectrometer (UV-spec) were used to sense precise fluid injections in the nano-Liter range. FIG. 9 shows four sequential views from a video of the invented microelectrode dispensing de-ionized water from the first of three ports.

Example 3

Combined Electrical Recording and Fluid Delivery

Once the devices were validated electrical and fluidically, they were implanted and both modes of operation were enabled simultaneously. In order to conduct such tests, the devices have to be assembled in a package compatible with chronic implantation. FIG. 10 shows two assembled devices attached to the skull, whereas the implantable electrode is connected to a printed circuit board (PCB) by way of an integrated flexible ribbon cable. A micro-tube and micro-connector are then connected to the backside of the PCB. A pump is connected to the micro-tube for fluid injection. A recording system is hooked up to the micro-connector for signal acquisition and processing. FIG. 10 shows two microelectrodes implanted into rat brain to test the microelectrodes' ability to deliver chemicals locally to an area monitored by recording sites. During the test, an excitatory neurotransmitter agonist (AMPA) was delivered for short periods of time while monitoring the discharge rate of a unit being picked up by a recording site located next to the fluid outlet.

Figure 11:
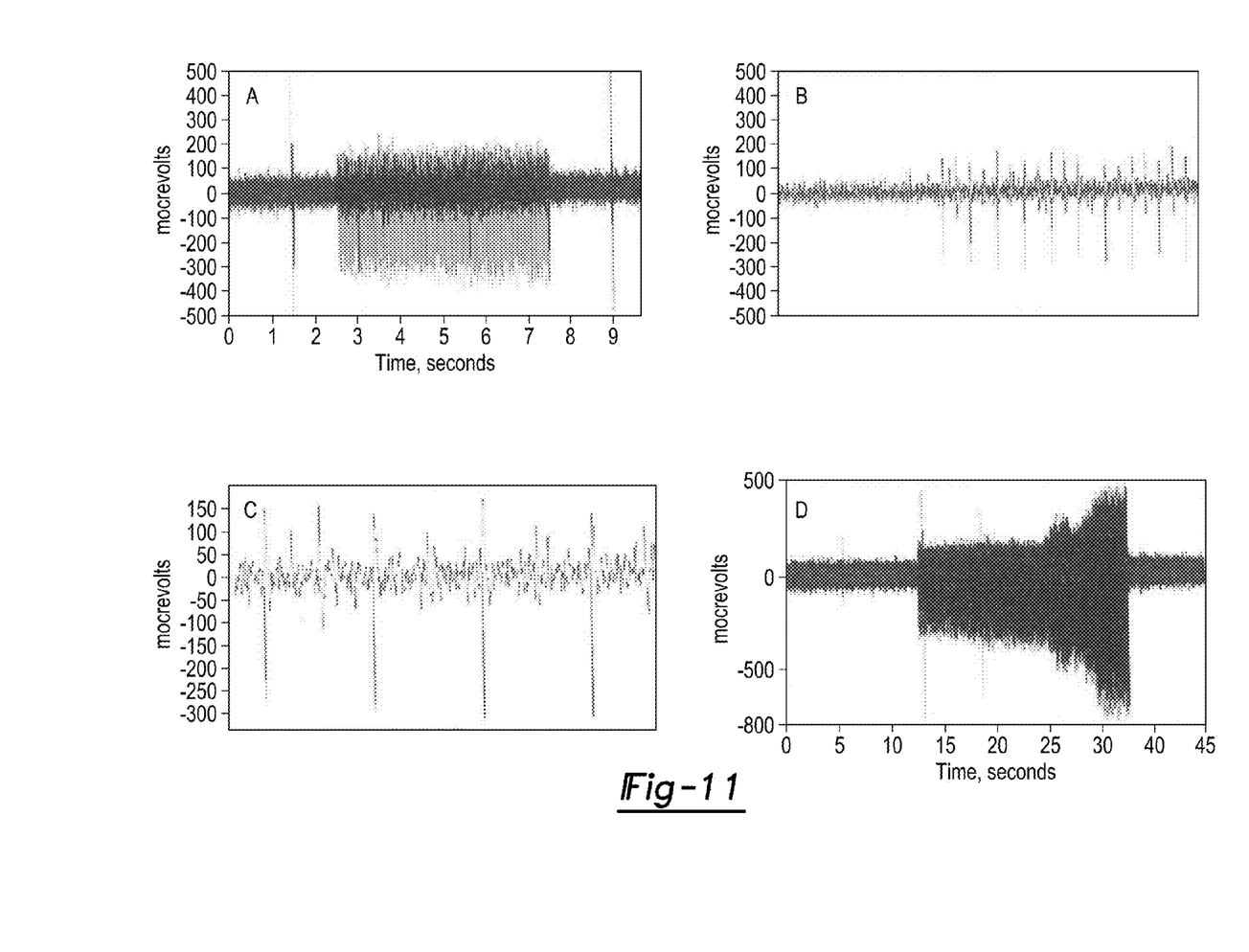
FIG. 11 shows electrical recordings during an acute surgery, showing results of an AMPA injection via an invented microelectrode into a rat brain

FIG. 11 shows the recordings of a signal from a neuron detected by a site near the fluid outlet. FIG. 11 demonstrates that the injection of AMPA affected the firing properties of the neurons being recorded from. The recorded outputs serve as evidence of the ability to selectively deliver chemicals locally to points in the CNS while recording the effects that the chemicals have on the firing rate of neurons local to the injection site.

All cited references are incorporated in full by reference as though fully set forth herein.

The preceding description has been presented only to illustrate and describe exemplary embodiments of the methods and systems of the present invention. It is not intended to be exhaustive or to limit the invention to any precise form disclosed. It will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, it is intended that the invention not be limited to the particular embodiment disclosed as the best mode contemplated for carrying out this invention, but that the invention will include all embodiments falling within the scope of the claims. The invention may be practiced otherwise than is specifically explained and illustrated without departing from its spirit or scope. The scope of the invention is limited solely by the following claims.

What is claimed is:

1. A microelectrode device for receiving and sending electrical signals within a nervous system of a subject, said microelectrode device comprising:
    a substantially-flexible planar shaft having a polymer-based substrate made of at least two flexible, planar thin-film polymer layers and at least one planar metallic layer, the substantially-flexible planar shaft having a proximal end and a distal end;
    a plurality of electrode sites disposed on the shaft, at least one of the plurality of electrode sites operable to output a stimulating signal to the nervous system and at least one of the plurality of electrode sites operable to record an electrical signal within the nervous system;
    at least one fluidic channel extending within the substantially-flexible planar shaft from the proximal end to generally the distal end, the at least one fluidic channel configured for the delivery of fluid to the nervous system,
    a fluid delivery system fluidly coupled to the at least one fluidic channel, the fluid delivery system configured to output the fluid to the at least one fluidic channel;
    a stimulating system operably coupled to the at least one of the plurality of electrode sites configured to output the stimulating signal; and
    a recording system operably coupled to the at least one of the plurality of electrode sites configured to record the electrical signal within the nervous system;
    wherein the outputting of the stimulating signal to the nervous system and the recording of the electrical signal within the nervous system are configured to occur simultaneously with the fluid being delivered to the nervous system.

2. The microelectrode device of claim 1, wherein the plurality of electrode sites and the at least one fluidic channel have respective connections compatible with the fluid delivery system, the stimulating system, and the recording system.

3. The microelectrode device of claim 1, wherein at least one of the plurality of electrode sites is disposed between the at least two flexible polymer layers.

4. The microelectrode device of claim 3, wherein the polymer-based substrate comprises at least five flexible thin-film polymer layers.

5. The microelectrode device of claim 1, wherein the at least one fluidic channel comprises a fluidic outlet and the substantially-flexible planar shaft further comprises a valve flap coupled to the fluidic outlet.

6. The microelectrode device of claim 5, wherein the valve flap is pressure-operated.

7. The microelectrode device of claim 1 wherein the fluid is a drug and the at least one fluidic channel is configured for the delivery of the drug to the nervous system.

8. The microelectrode device of claim 7 wherein the drug is delivered to the nervous system simultaneously with the outputting the stimulating signal to the nervous system, the recording electrical signal within the nervous system is responsive to affects caused by at least one of the delivery of the drug and the outputting the stimulating signal.

9. The microelectrode device of claim 1 wherein the at least one planar metallic layer is immediately adjacent to the at least one fluidic channel.

10. The microelectrode device of claim 1 wherein the at least one fluidic channel is further configured to extract fluid from the nervous system.

11. A method of using a microelectrode device for receiving and electrical signal sending electrical signals within a nervous system of a subject, the method comprising the steps of:
    providing a substantially-flexible planar shaft having a polymer-based substrate made of at least two flexible, planar thin-film polymer layers and at least one planar metallic layer, the substantially-flexible planar shaft having a proximal end and a distal end;
    providing a plurality of electrode sites disposed on the shaft, at least one of the plurality of electrode sites operable to output a stimulating signal to the nervous system and at least one of the plurality of electrode sites operable to record an electrical signal within the nervous system; and
    providing at least one fluidic channel extending within the substantially-flexible planar shaft from the proximal end to generally the distal end, the at least one fluidic channel configured for the delivery of fluid to the nervous system; and
    delivering the fluid to the nervous system simultaneously with outputting the stimulating signal to the nervous system and recording electrical signals within the nervous system.

12. The method in claim 11, wherein the at least one fluidic channel is configured to extract fluids from the nervous system.

13. The method of claim 11, wherein at least one of the plurality of electrode sites is disposed between the at least two flexible polymer layers.

14. The method of claim 11, wherein the polymer-based substrate comprises at least five flexible thin-film polymer layers.

15. The method of claim 11, wherein the at least one fluidic channel comprises a fluidic outlet and the substantially-flexible planar shaft further comprises a valve flap coupled to the fluidic outlet, the valve flap being actuated in response to pressure of the fluid.

16. The method of claim 11 wherein the step of delivering the fluid to the nervous system simultaneously with outputting the stimulating signal to the nervous system comprises delivering a drug to the nervous system simultaneously with outputting the stimulating signal to the nervous system; and
recording electrical signals within the nervous system responsive to affects caused by the delivering the drug to the nervous system.

17. The method of claim 11 wherein the at least one planar metallic layer is immediately adjacent to the at least one fluidic channel.

18. A microelectrode device for receiving and sending electrical signals within a nervous system of a subject, said microelectrode device comprising:
a substantially-flexible planar shaft having a polymer-based substrate made of at least two flexible, planar thin-film polymer layers and at least one planar metallic layer, the substantially-flexible planar shaft having a proximal end and a distal end, the at least one planar metallic layer being positioned between the at least two flexible polymer layers and immediately adjacent the at least one fluidic channel;
a plurality of electrode sites disposed on the shaft, at least one of the plurality of electrode sites operable to output a stimulating signal to the nervous system and at least one of the plurality of electrode sites operable to record an electrical signal within the nervous system; and
at least one fluidic channel extending within the substantially-flexible planar shaft from the proximal end to generally the distal end, the at least one fluidic channel configured for the delivery of fluid to the nervous system,
a fluid delivery system fluidly coupled to the at least one fluidic channel, the fluid delivery system configured to output the fluid to the at least one fluidic channel;
a stimulating system operably coupled to the at least one of the plurality of electrode sites configured to output the stimulating signal; and
a recording system operably coupled to the at least one of the plurality of electrode sites configured to record the electrical signal within the nervous system;
wherein the outputting of the stimulating signal to the nervous system and the recording of the electrical signal within the nervous system are configured to occur simultaneously with the fluid being delivered to the nervous system.

19. The microelectrode device of claim 18, wherein at least one of the plurality of electrode sites is disposed between the at least two flexible polymer layers.

20. The microelectrode device of claim 18 wherein the fluid is a drug and the at least one fluidic channel is configured for the delivery of the drug to the nervous system.

* * * * *